United States Patent [19] [11] 4,073,725
Takeuchi et al. [45] Feb. 14, 1978

[54] METHOD AND APPARATUS FOR LIQUID CHROMATOGRAPHY UNDER ELEVATED PRESSURE

[75] Inventors: Seiji Takeuchi, Hitachiota; Kazunori Fujita, Ibaraki; Ikuo Shimokobe, Hitachi, all of Japan

[73] Assignee: Hitachi, Ltd., Japan

[21] Appl. No.: 679,750

[22] Filed: Apr. 23, 1976

[30] Foreign Application Priority Data

May 9, 1975 Japan ............................ 50-54466
May 19, 1975 Japan ............................ 50-58515

[51] Int. Cl.² ............................................ B01D 15/08
[52] U.S. Cl. ............................ 210/31 C; 210/198 C
[58] Field of Search ............ 210/31 C, 198 C, 31 R, 210/32; 73/61.1 C; 23/230 R, 253 R

[56] References Cited

U.S. PATENT DOCUMENTS

| 3,686,118 | 8/1972 | Benson | 210/31 C |
| 3,847,550 | 11/1974 | Scott et al. | 210/31 C |
| 3,897,213 | 7/1975 | Stevens | 210/31 C |
| 3,905,903 | 6/1975 | David | 210/31 C |
| 3,923,460 | 12/1975 | Parrott et al. | 210/31 C |
| 3,925,019 | 12/1975 | Small et al. | 210/31 C |

OTHER PUBLICATIONS

Introduction to Modern Liquid Chromatography by Snyder and Kirkland, John Wiley and Sons, New York, N. Y., pp. 299-301 and 309, 1974.

Primary Examiner—John Adee
Attorney, Agent, or Firm—Craig & Antonelli

[57] ABSTRACT

A sample containing a plurality of components to be analyzed is introduced to a separation column at its top through a sample feeding device. The sample thus introduced is separated to the individual components in the separation column. Ion exchange resins capable of undergoing deformation depending upon an applied pressure are filled in the separation column. An eluting solution containing sodium ions is fed to the separation column at its top under a pressure of 40 kg/cm² or higher through a feed pump. Components leaving the separation column at its bottom are detected by a detector. After the components have left the separation column, a regenerating solution containing lithium ions is introduced to the separation column at its bottom, and is made to leave the separation column at its top. The ion exchange resins are regenerated by passing the regenerating solution through the separation column, and a separation for another sample is made ready thereby. Another sample is then introduced into the separation column at its bottom and the separated components of the sample are made to leave the separation column at its top.

15 Claims, 4 Drawing Figures

METHOD AND APPARATUS FOR LIQUID CHROMATOGRAPHY UNDER ELEVATED PRESSURE

The present invention relates to a method and apparatus for liquid chromatography, and more particularly to a method and apparatus suitable for high speed separation of a sample, using a column filled with ion exchange resins and an analytical system under an elevated pressure.

A liquid chromatographic separation column is generally filled with ion exchange resins. When a sample is eluted and developed in such a separation column, the sample and an eluting solution are introduced into the column at its top, and a column-regenerating solution is also introduced into the column at its top. Recently, it has been attempted to speed up sample separation in the liquid chromatography, and, for example, a liquid chromatographic apparatus capable of measuring 20 amino acids as protein constituents within 70 minutes has been commercially available up to now. The present inventors tried to make further improvement of said liquid chromatographic apparatus and succeeded in the measurement within 40 minutes. However, the high speed measurement is attained only by using very fine fillers or a column having a small inner diameter, and thus the analytical system is inevitably exposed to an increased pressure such as several 10 to several 100 kg/cm$^2$. The increased pressure has brought a new problem.

Explanation will be made below, by way of a method for analyzing amino acids as an example of the liquid chromatography. When separation and measurement of 20 amino acids as the protein constituents are to be completed within 40 minutes, the pressure at the inlet of the separation column exceeds 50 kg/cm$^2$. In the case of analyzing amino acids, 8 – 18% cross-linked styrene-divinylbenzene copolymers are generally used as the ion exchange resins to be filled in the separation column. However, when the pressure at the inlet of the separation column exceeds about 40 kg/cm$^2$, the degree of contraction of the resins becomes extremely large, giving an adverse effect upon the separation of the components in samples. This fact has been confirmed by the present inventors through the following experiment.

Into a separation column were filled 10% cross-linked, strongly acidic cation exchange resins. Temperature of the separation column was kept at 60° C. The initial pressure at the column inlet just after the separating conditions were set was set to be about 55 kg/cm$^2$. Both eluting solution and regenerating solution were continuously introduced into the column only at the top, and the pressure at the column inlet was measured 4 hours after the separating conditions were set, and found to be 7 – 10 kg/cm$^2$ higher than the initial pressure. Peaks of threonine and serine, which are very close to each other among 20 amino acids, were taken into account, and percent separations of these two (ratio of depth to the bottom between peaks) were calculated. The percent separation was 78% just after the separating conditions were set (A), and 64% 4 hours after the separating conditions were set (B). Separation coefficients of threonine and serine (ratio of retention time) were measured, and found to be 1.10 for (A), and 1.09 for (B). To increase the separation coefficient 1.09 to 1.10, it was necessary to increase a column length by 20%.

As is well known, a peak area is measured in chromatography to quantitatively determine a content of a component. To obtain a measured value with a high preciseness, it is necessary to assure a percent separation of more than 70%. In said case (B), no satisfactory measurement preciseness is obtained. Increase in the pressure at the column inlet after the measuring conditions are set, and changes in the percent separation in the continuous operation are due to the contraction of the resins and the resulting change in resin characteristics. The change in the resin characteristics will have the same result with time as when the degree of cross-linking of resins is increased.

In the present invention, it is one of essentials to reverse the direction of an eluting solution and a regenerating solution to be passed through a separation column to each other. So far as the reverse direction is concerned, it is disclosed in U.S. Pat. No. 3,220,164, entitled "Recirculation Chromatography". Said prior art reference discloses a structure of successively connecting a plurality of columns in series for attaining one component separation, continuously and repeatedly passing a sample through at least two columns, and successively washing the columns one by one during the recirculation. However, the prior art reference nowhere teaches the subject matter of the present invention.

Heretofore, such problems as reduction in the percent separation or deterioration of reproducibility under high inlet pressure of the separation column, for example, 40 to 50 kg/cm$^2$ or above, have not been recognized yet.

One object of the present invention is to provide a method and apparatus for liquid chromatography without any reduction in reproducibility even in a continuous operation for a prolonged time under a high pressure.

Another object of the present invention is to provide a method and apparatus for liquid chromatography capable of performing a continuous operation for a prolonged time while maintaining an analytical system under a high pressure above 40 kg/cm$^2$.

Other object of the present invention is to provide a method and apparatus for liquid chromatography capable of readily eliminating the impurities introduced into a separation column during the separation.

Still other object of the present invention is to provide a method and apparatus for restoring ion exchange resins deformed under a high pressure to the original state in the separation column.

Further object of the present invention is to provide a method and apparatus for liquid chromatography capable of conducting separation of a sample and regeneration of a column in parallel, that is, the method and apparatus having less time loss in continuous measurement.

Still further object of the present invention is to provide a method and apparatus for eliminating changes in characteristics by swelling ion exchange resins, contracted during the service under a high pressure, for a short time.

According to the present invention, a proper combination of counter ions contained in an eluting solution and ions contained in a column-regenerating solution is made. Ions, which have the same electric charge as that of the counter ions in the eluting solution and have a larger hydration number, are made present in the regenerating solution.

According to a preferable mode of carrying out the present invention, a separation column filled with ion exchange resins deformable under pressure is used, and an eluting solution is fed to the column under a high pressure of 40 kg/cm² or higher. The eluting solution and a regenerating solution are fed to the separation column, but in a continuous operation, a period of feeding the eluting solution and the regenerating solution in a specific direction to the column, and a period of feeding them in a direction opposite to the specific direction are periodically alternated. That is, an inlet of column, which is at the upstream side in the initial period, will be at the downstream side in the next period. That is, the resins, which are contracted under a high pressure at the upstream side, are released from the high pressure in the next period, and swelling of the contracted resins is promoted thereby.

Other objects and features of the present invention than those described above will be apparent from the following detailed description, referring to the accompanying drawings.

Explanation will be made, first of all, of the test results obtained by the present inventors before an explanation of the Examples of the present invention is made. The tests were made to investigate the state of change in resin characteristics when the eluting solution and the regenerating solution were fed to the separation column always in the same directions.

The eluting solution was a monochloroacetic acid buffer solution containing 1.0 M sodium ion ($Na^+$) and 0.145 M zinc ions ($Zn^{2+}$), at a pH of 3.0. At first, the eluting solution was passed through the separation column, whereby the zinc ion concentration of the eluting solution was brought in an equilibrium state with strongly acidic cation exchange resins in the column. The initial pressure at the column inlet was set to about 30 kg/cm². Four hours after having been kept under an increased pressure, the resins that have adsorbed the zinc ions were taken out of the separation column at the upper stage, middle stage, and lower stage of the column as three separate layers. Table 1 shows volumes of settled-down resins of the individual layers, and amounts of zinc ions adsorbed per 1 ml of the resins, which were measured by the present inventors.

Table 1

| Position of the resins in column | Volume of settled-down resins (ml) | Amount of zinc ions adsorbed per 1 ml of the resins (mg) |
|---|---|---|
| Upper stage | 12.2 | 7.93 |
| Middle stage | 11.1 | 8.72 |
| Lower stage | 13.3 | 8.91 |

It is seen from the results of Table 1 that even under the initial pressure of 30 kg/cm² the amount of zinc adsorbed on the resin layer is smaller at the upper stage of the column, that is, where the pressure load is higher. The difference is more remarkable in the amount of the adsorbed zinc under much higher initial pressure.

Figure 1:
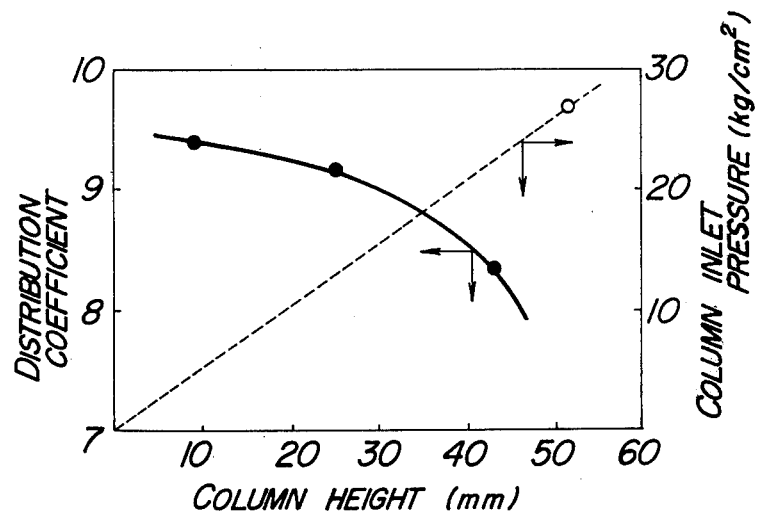
FIG. 1 is a graph showing relations between column height and distribution coefficient, and relations between column height and column inlet pressure.

FIG. 1 shows relations between the column height and distribution coefficient, and relations between the column height and column inlet pressure, based on the results of Table 1. In that case, the distribution coefficient is a ratio of the amount of metal ions in the resin layer to the amount of the same metal ions in the eluting solution, and it is desirable that the distribution coefficient takes a constant value even if the column height is changed. It is apparent from the foregoing test results that the distribution coefficient is lowered with increasing column height, that is, with increasing column inlet pressure.

The present invention has been made on the basis of findings that ion exchange resins have a hydroscopic property, and ions have different hydration numbers, depending upon the kinds of ions. Ions exist in a state of combination with water molecules, that is, the so-called hydrated state, in an aqueous solution, and the number of hydrating water molecules depends upon the kinds of ions. Generally, it is known that the sizes of hydrated ions become larger, if the ions have smaller sizes. Fixed ions or counter ions in the ion exchange resins also exist in a hydrated state, and the water content and volume in water of resins depend upon the kinds of ions.

Table 2 shows specific volumes in dry state and volumes in water of salt form resins.

Table 2

|  | HR | LiR | NaR | NH₄R | KR |
|---|---|---|---|---|---|
| Volume in water (ml/g) | 1.524 | 1.503 | 1.418 | 1.409 | 1.357 |
| Dry volume (ml/g) | 0.696 | 0.702 | 0.730 | 0.792 | 0.763 |

In Table 2, HR, LiR, NaR, NH₄R and KR represent resins in a hydrogen form, lithium form, sodium form, ammonium form, and potassium form, respectively. The volumes in water of the resins in the salt forms become larger in the order of $K < NH_4 < Na < Li < H$. The water contents of the resins become higher in the order of $K \leq NH_4 < Na < Li < H$.

Hydration numbers of the individual ions are 0.6 for K, 0.2 for NH₄, 2.0 for Na, 3.4 for Li and 3.9 for H, and the resins with ions having a larger hydration number have a higher water content.

When sodium ions are contained in the eluting solution as the counter ions, the resins can be rapidly swollen by using an aqueous lithium hydroxide solution containing lithium ions having a larger hydration number than that of the sodium ions, as a regenerating solution. When one analysis is completed, using sodium ions as the counter ions in the eluting solution, and then when an aqueous lithium hydroxide solution is used as the regenerating solution, the height of the resin layer can be restored to the original in 18 minutes. It is preferable that both counter ions and ions in the regenerating solution are alkali metal ions.

When $K^+$ is used as the counter ions in the eluting solution, only $Na^+$, or only $Li^+$, or both $Na^+$ and $Li^+$ must be contained in the regenerating solution. The counter ions are not restricted to a single ion species, and, for example, can include both $Na^+$ and $K^+$. Similarly, the alkali metal ions contained in the regenerating solution is not restricted to a single alkali metal ion species.

Figure 2:
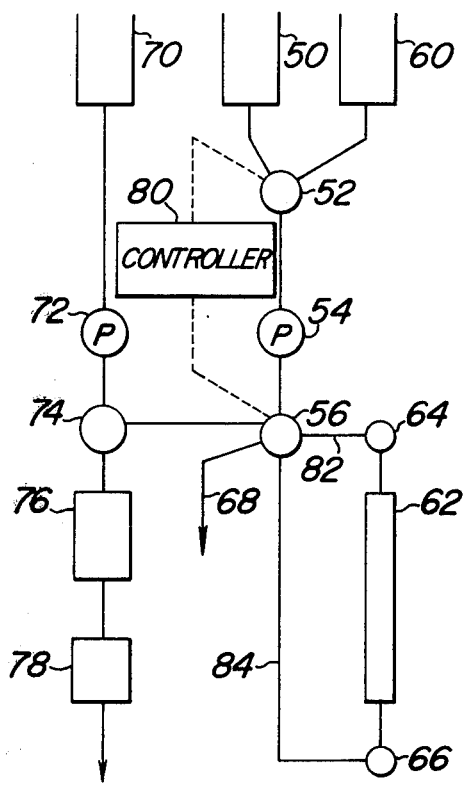
FIG. 2 is a schematic flow diagram of one embodiment of the present invention.

One embodiment of the present invention will be described below, referring to FIG. 2.

In a separation column 62, strongly acidic cation exchange resins, for example, styrene-divinylbenzene copolymers having a degree of cross-linking of 6 to 16%, are packed. Particle diameters of the copolymers are in a range of 5 to 8 $\mu$. The inner diameter of the separation column 62 is 7 mm, and the height of the resin layer is 135 mm. Sample feeding means 64 and 66 are provided before and after the separation column 62, respectively, and are connected to a switch valve 56. In an eluting solution tank 50, an eluting solution comprising a citric acid buffer solution having a pH of 3.25 is placed. The eluting solution contains 0.20 M sodium ions as counter ions.

In a regenerating solution tank 60, a regenerating solution comprising an aqueous lithium hydroxide solution is placed. The eluting solution tank 50 and the regenerating solution tank 60 are connected to a switch valve 52, and a feed pump 54 is provided in a line between the switch valve 52 and the switch valve 56. The switch valves 52 and 56 are interlocked with each other, and a timing to switch one of these switch valves to another is controlled by a controller 80. A reagent tank 70 containing a ninhydrine coloring agent is connected to a mixing section 74 through a feed pump 72. A reaction tank 76 keeps a mixture solution at a predetermined temperature for a predetermined period of time, and thus is comprised of a long pipe provided in a thermostat tank. A detector 78 is comprised of an effluent photometer. A discharge outlet 68 is connected to the switch valve 56.

The separation column 62 has a jacket, and water at a constant temperature is circulated through the jacket to keep the separation column at 60° C. Actually, a plurality of the eluting solution tanks are provided, but in the present description only one eluting solution tank is shown for brevity of explanation. Flow rate of the eluting solution is set to be 1.2 ml/min. 30 minutes after the start of operation, the column inlet pressure amounts to 55 kg/cm², and the reaction tank 76 is kept at 100° C.

According to instructions from the controller 80, the driving mechanisms of the switch valves 52 and 56 are actuated, and the eluting solution from the eluting solution tank 50 is fed through a passage 82. An amino acid sample injected from a sample feeding means 64 is eluted and developed in the column 62. Effluent liquid from the column 62 passes through a passage 84, and reaches the mixing section 74 through the switch valve 56. In the mixing section 74, the effluent liquid is mixed with the coloring reagent fed by the pump 72. The amino acid components in the mixed liquid are subjected to sufficient coloring during the passage through the reaction tank 76, and light absorbancy is measured by the detector 78. Two measuring wave lengths are used, i.e. 440 mm and 570 mm. Changes in the light absorbancy is converted to electric signals, and depicted as a chromatogram on a recorder. Contents of the individual amino acid components are determined from peak positions and areas for the individual components.

Then, the switch valves 52 and 56 are switched over, and the regenerating solution tank 60 is communicated with the pump 54, and the pump 54 is then communicated with the passage 84. At that time, the passage 82 is communicated with the discharge outlet 68. The regenerating solution is fed to the column 62 through the passage 84, and discharged from the discharge outlet 68 through the passage 82. The inlet, which is at the upstream side when the eluting solution is passed through the column, is now at the downstream side, and thus the resins contracted under the increased pressure is now released from the pressure, and swollen. There is a pressure gradient between the inlet and the outlet in the column packed with the resins, and a maximum pressure prevails at the inlet of the column, but approximately atmospheric pressure prevails at the outlet. When the inlet and the outlet are interchanged during the continuous operation under the increased pressure, the pressure load within the column can be averaged.

Then, the switch valves 52 and 56 are switched over, and the eluting solution is fed to the separation column 62 through the passage 84. The eluting solution leaving the column 62 is discharged from the detector 78 successively through the passage 82, switch valve 56, mixing section 74, and reaction tank 76, whereby the eluting solution and the resin layer are brought into an equilibrium.

A second sample is introduced to the column from the sample feeding means 66. The eluting solution is fed to the column through the passage 84. After the second separation, the switch valves 52 and 56 are switched over, and the regenerating solution is fed to the column 62 through the passage 82. A third sample is fed to the column from the sample feeding means 64.

At the sample separation, impurities in the sample are retained around the upstream side inlet of the column, but since the regenerating solution is made to pass through the column in a direction opposite to that of the preceding eluting solution after the separation, the impurities can be simply removed. When the eluting solution and the regenerating solution are passed through the column always in the same directions, the impurities cannot be sufficiently removed during the regenerating period.

Figure 3:
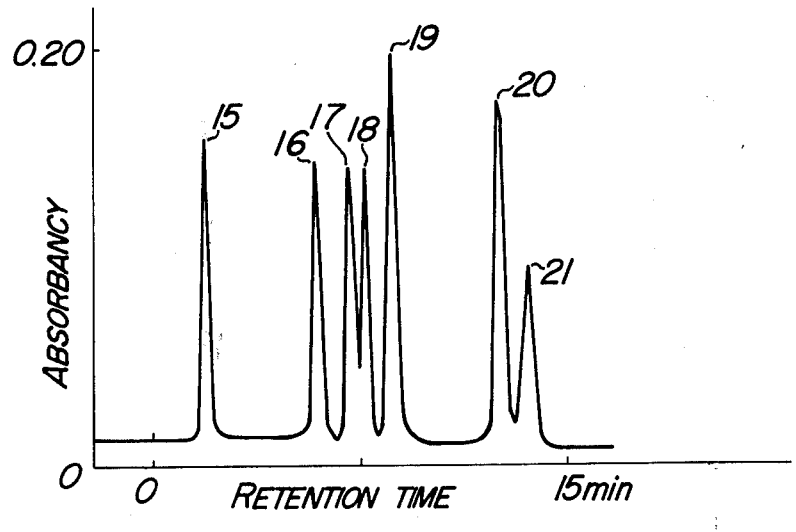
FIG. 3 is an illustration of a chromatogram of a sample measured according to the present invention.

In FIG. 3, an example of chromatogram of a sample obtained according to the foregoing embodiment is shown, where peaks each of cystine sulfonic acid 15, aspartic acid 16, threonine 17, serine 18, glutamic acid 19, glycine 20 and alanine 21 are given. The chromatogram is the one obtained 10 hours after the start of continuous operation, and the percent separation of threonine 17 and serine 18 is the same 78% as just after the start of the operation. The column inlet pressure can be maintained constantly at about 55 kg/cm² during the continuous operation. According to the present invention, the swelling of the resins is promoted by the alkali metal ions in the regenerating solution, and thus any change in the percent separation due to the contraction of the resins can be substantially suppressed, and measurements can be made with a good reproducibility.

Figure 4:
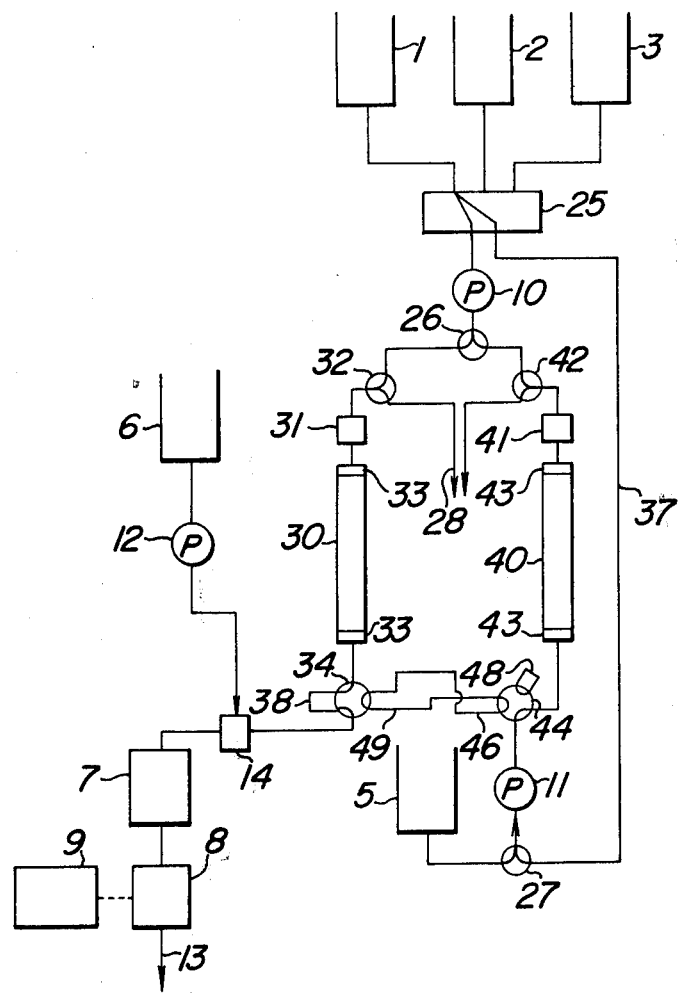
FIG. 4 is a schematic flow diagram of an other embodiment of the present invention.

In FIG. 4, a schematic flow diagram of another embodiment of the present invention is shown. In eluting solution tanks 1, 2 and 3, eluting solutions having different metal ion concentrations and pHs are placed, individually. Any of these eluting solutions contains sodium ions as counter ions. In a regenerating solution tank 5, an aqueous lithium hydroxide solution is placed. In a reagent tank 6, a ninhydrine reagent solution for coloring amino acids is placed. Actions of switch valves 25, 26, 27, 32, 34, 42, and 44 are controlled by a controller (not shown in the drawing) for controlling driving mechanisms of these valves according to a predetermined program. Column fillers are styrene-divinylbenzene copolymers.

Two separation columns 30 and 40 provided in parallel with each other are provided with filters 33 and 43 at both ends of the columns, respectively, and sample feeding devices 31 and 41 are connected to one-side ends of the columns 30 and 40, respectively. Structure of a mixing section 14 for mixing the coloring agent to be fed from the coloring agent tank 6 by a feeding pump 12 with an effluent liquid from the columns, reaction tank 7 for reaction of amino acids, detector 8, etc. are the same as that of the foregoing embodiment as described referring to FIG. 2.

An eluting solution to be used is selected by the switch valve 25, and the eluting solution can be switched to another even in the course of sample separation. The eluting solution is fed to the separation column 30 through the switch valves 26 and 32 by an eluting solution feed pump 10, and the packed resin layer and the eluting solution are brought into an equilibrium state. A sample is fed to the column 30 from the sample feeding device 31, and separated in the column 30. The eluting solution containing separated components is passed through a six-way switch valve 34 having a passage 38, and mixed with the ninhydrine coloring agent in the mixing section 14, and coloring reaction is promoted in the reaction tank 7. Changes in the light absorbancy of the colored components are measured by the detector 8, for example, effluent photometer, using two wave lengths, 440 nm and 570 nm, and the effluent eluting solution is discharged from an outlet 13. The changes in the light absorbancy is converted to electric signals, and depicted as a chromatogram on a recorder 9. In the course of separation, the switch valve 25 is switched over.

During the sample separation in the separation column 30, the separation column 40 is made ready for separation of another sample. That is, the regenerating solution from the regenerating solution tank 5 through the switch valve 27 is fed to the column 40 at the lower end through a six-way switch valve 44 by a feed pump 11. The regenerating solution passed through the column 40 is discharged from a discharge outlet 28 through the switch valve 42. After the regenerating solution is passed through the column 40 from the lower end upwards for a predetermined period of time, the switch valve 27 is switched over, and the eluting solution is fed to the column 40 at the lower end through the passage 37, whereby the resins in the column 40 and the eluting solution are brought into an equilibrium state. The eluting solution is discharged from the discharge outlet 28 through the switch valve 42.

When the separation of the sample is completed in the separation column 30, the six-way switch valves 34 and 44, and the switch valves 26, 32, 42, and 27 are switched over. Thus, the eluting solution to be fed by the eluting solution feed pump 10 is fed to the separation column 40 at the top end through the switch valves 26 and 42 by said switching-over, and a sample is also fed to the separation column 40 from the sample feeding device 41. The eluting solution containing components separated through the column 40 is fed to the detecting system through a passage 48 of the six-way switch valve 44, connection passage 49 and the six-way switch valve 34. During the sample separation in the separation column 40, the regenerating solution from the regenerating solution tank 5 is fed to the column 30 at the lower end by the feed pump 11. The regenerating solution is discharged from the discharge outlet 28 through the pump 11, six-way switch valve 44, connection passage 46, six-way switch valve 34, column 30 and switch valve 32. After the regenerating solution is passed through the column 30 for a predetermined period of time, the switch valve 27 is switched over, and the eluting solution from the passage 37 is fed to the column 30 at the lower end, and discharged from the discharge outlet 28. Then, the switch valves in the flow passage system are switched over to the original state, and a third sample is separated in the separation column 30.

In the present embodiment, the sample and the eluting solutions are always fed to the columns at the upper ends, and the regenerating solution and the eluting solution for equilibration are always fed to the columns at the lower ends. Separation of the sample and regeneration of the column are carried out in parallel, and thus there is less time loss in the continuous measurement. The column upstream inlet for the eluting solution, which is at the upstream side at the preceding sample separation, is at the downstream side for the regenerating solution at the regeneration, and thus, the resins approximately around the column upstream side outlet, which are contracted under the increased pressure at the sample separation, are released from the increased pressure at the regeneration, and are swollen. The alkali metal ions in the regenerating solution also contribute to the swelling of the resins. Therefore, the same column characteristics as at the preceding sample separation can be reproduced at the succeeding sample separation. The impurities existing approximately around the upstream-side inlet can be readily removed in a short time by the regenerating solution. In the foregoing embodiment, a continuous operation can be carried out for a prolonged time while maintaining the analytical system under the increased pressure. The present invention can be particularly effectively applied to an analytical system under a pressure of 40 kg/cm$^2$ or more.

What is claimed is:

1. A method for liquid chromatography for high pressure separation, which comprises:
   feeding a sample to be separated to components to a separation column packed with an ion exchange resin deformable under pressure,
   feeding an eluting solution containing counter ions to the separation column,
   detecting a plurality of the components leaving the separation column, and
   feeding a regenerating solution containing metal ions having the same electric charge as that of the counter ions and a larger hydration number than that of the counter ions to the separation column to regenerate the ion exchange resin.

2. A method according to claim 1, wherein a flow direction of the eluting solution to be fed to the separation column is opposite to a flow direction of the regenerating solution to be fed to the separation column.

3. A method according to claim 2, wherein the eluting solution is fed to the separation column always at one end, and the regenerating solution is fed to the separation column always at an opposite end.

4. A method according to claim 2, wherein after the regenerating solution and the eluting solution are fed to the separation column at one end, the regenerating solution and the eluting solution are fed to the separation column at an opposite end.

5. A method according to claim 1, wherein the eluting solution contains sodium ions as the counter ions, and the regenerating solution contains lithium ions.

6. A method according to claim 1, wherein the eluting solution contains potassium ions as the counter ions, and the regenerating solution contains at least one of sodium ions and lithium ions.

7. A method according to claim 1, wherein the ion exchange resins are styrene-divinylbenzene copolymers.

8. A method according to claim 1, wherein pressure at an inlet end of the separation column is maintained at 40 kg/cm² or greater.

9. A method for liquid chromatography for high pressure separation which comprises:
providing an eluting solution containing alkali metal counter ions to a separation column packed with a cation exchange styrene-divinylbenzene resin deformable under pressure to bring said solution and said resin into an equilibrium state;
providing a sample containing amino acids to be separated into components to the separation column;
providing the eluting solution containing alkali metal counter ions to the separation column to elute said sample;
detecting a plurality of sample components separated by flow of the sample through the column;
providing a regenerating solution containing alkali metal ions having a same electric charge as that of the counter ions and a greater hydration number than that of the counter ions to the separation column to regenerate the cation exchange resin, the regenerating solution being provided to an end of the separation column opposite an end to which the amino acid sample is previously provided.

10. A method according to claim 9, wherein pressure at an inlet end of the separation column is maintained at 40 kg/cm² or greater.

11. A method according to claim 9, wherein two of said separation columns in parallel are used to separate the sample into components by effecting the steps of (a) providing the regenerating solution to a first separation column through a first inlet end followed by
(b) providing the eluting solution to the first separation column through the first inlet end to bring the eluting solution and the resin to a state of equilibrium; simultaneously with steps (a) and (b)
(c) providing the sample containing amino acids to a second separation column at a second inlet end and
(d) providing the eluting solution to the second separation column at the second inlet end to elute the sample; and
subsequent to elution of components of said sample in the second separation column, effecting sequentially the providing of the regeneration solution and the eluting solution of steps (a) and (b) at the same end of the second separation column while simultaneously effecting the providing of the sample and the eluting solution of steps (c) and (d) at the same end of the first separation column.

12. A method according to claim 11, wherein pressure at an inlet end of the first and second separation columns is maintained at 40 kg/cm² or greater.

13. A method according to claim 12, wherein the sample and the eluting solution for elution of the sample are provided to the first and second separation columns at an inlet at an upper end, and the regenerating solution and the eluting solution for equilibration are provided to the first and second separation columns at an inlet at a lower end.

14. A method according to claim 11, wherein the eluting solutions contain sodium ions as the counter ions and the regenerating solution contains lithium ions.

15. A method according to claim 11, wherein the eluting solutions contain potassium ions as the counter ions and the regenerating solution contains at least one of sodium ions or lithium ions.

* * * * *